United States Patent [19]

McBride

[11] Patent Number: 4,683,897

[45] Date of Patent: Aug. 4, 1987

[54] ELECTRIC NAIL FILING DEVICE

[76] Inventor: Julia K. McBride, 8910 Second St., Lanham, Md. 20706

[21] Appl. No.: 731,757

[22] Filed: May 8, 1985

[51] Int. Cl.⁴ .............................................. A45P 29/05
[52] U.S. Cl. ....................................... 132/73.6; 132/73
[58] Field of Search ..................... 132/73, 73.5, 73.6, 132/75.6, 75.8, 76.2, 76.4

[56] References Cited

U.S. PATENT DOCUMENTS

| | | | |
|---|---|---|---|
| 1,181,020 | 4/1916 | Lapetina | 132/75.8 |
| 1,482,837 | 2/1924 | Buck | 132/75.8 |
| 1,822,631 | 9/1931 | Roig | 15/23 |
| 1,869,197 | 7/1932 | Holz | 132/75.8 |
| 1,892,867 | 1/1933 | Burr | 132/73.6 |
| 1,915,305 | 6/1933 | Gallagher | 132/75.8 |
| 2,056,379 | 10/1936 | Acocella | 132/73.6 |
| 2,376,946 | 5/1945 | Stinson | 132/76.5 |
| 2,533,106 | 12/1950 | Grover | 15/23 |
| 2,840,837 | 7/1958 | Gustems | 15/23 |
| 2,923,303 | 2/1960 | Hundt | 132/75.8 |
| 3,126,021 | 3/1964 | May | 132/76.4 |
| 3,216,034 | 9/1965 | Johnson | 15/23 |
| 3,311,117 | 3/1967 | Thompson | 132/73.6 |
| 3,420,250 | 1/1969 | Holmes | 132/73.6 |
| 3,451,086 | 6/1969 | Burgett | 15/23 |
| 3,596,667 | 8/1971 | Buercklin | 132/73.6 |
| 3,754,556 | 8/1972 | Watkins | 132/73.6 |
| 4,103,694 | 8/1978 | Burian | 132/73.6 |
| 4,137,926 | 2/1979 | Pao | 132/73.6 |
| 4,163,300 | 8/1979 | Quint | 15/23 |
| 4,275,749 | 6/1981 | Caroll | 132/11 A |
| 4,335,480 | 6/1982 | Poo-Sung | 15/23 |
| 4,344,202 | 8/1982 | Hayat | 15/23 |
| 4,408,623 | 10/1983 | Murray | 132/73.6 |

Primary Examiner—John J. Wilson
Attorney, Agent, or Firm—Browdy and Neimark

[57] ABSTRACT

An electric fingernail or toenail filing device includes a rotatable filing member having a fine particulated abrasive surface, and a protective skin guard for shielding the skin adjacent the nail from damage by the rotationg filing member when the device is in use. The filing member is tapered toward its end tip and preferably pine cone shaped. The device is preferably battery operated, lightweight and small to insure easy maneuverability in handling and convenient portability in storage.

10 Claims, 4 Drawing Figures

ELECTRIC NAIL FILING DEVICE

FIELD OF THE INVENTION

The present invention relates to electric nail filing devices, and more particularly to an electric nail filing device which includes a protective skin guard.

BACKGROUND OF THE INVENTION

Manicuring or pedicuring devices for filing fingernails and toenails are well known. The most popular such device is a standard flat nail file or emery board. These devices have the disadvantage of being manually powered. Furthermore, they cannot do an adequate job of reaching all of the surfaces needing smoothing, particularly for persons with curved fingernails or toenails. Toenails of substantial curvature cause substantial problems in obtaining effective smoothing of the outer edge, particularly when using a flat nail file.

Electrically operated manicuring and pedicuring devices are also part of the prior art. For example, U.S. Pat. No. 4,408,623 to Murray shows a battery powered manicuring device with a reciprocating flat manicuring implement. U.S. Pat. No. 1,892,867 to Burr shows a similar electrically powered reciprocating flat manicuring element. Although electrically powered, these devices suffer the same defects as do flat nail files or emery boards insofar as curved nails are concerned.

U.S. Pat. Nos. 3,126,021 to May and 4,137,926 to Pao show electrically rotary driven cylindrical grinding surfaces on nail trimming devices. The latter is portable and battery operated. These devices also suffer disadvantages. A cylindrical shape grinding surface will not permit easiest access to nails of various shapes, curvatures and sizes. Furthermore, these devices pose a significant risk of damage to the skin adjacent the nail during use.

While several patents in the prior art disclose the general concept of protective guards associated with powered rotating manicuring devices, none of the devices of such prior patents permit filing or smoothing of rough fingernails or toenails, particularly those with substantial curvature, without fear of damage to the adjacent skin. For example, U.S. Pat. No. 1,915,305 to Gallagher discloses a rotating disk-shaped nail file with a guard over the flat rotating surface thereof having slots therein for insertion of the fingernail. This is not particularly useful for curved nails. U.S. Pat. No. 2,056,379 to Acocella shows a rotating cylindrical filing device with a guard surrounding it except for an opening for insertion of the nail. Again, this is not suitable for all shapes and sizes of nails. Other types of guards are exemplified by U.S. Pat. Nos. 2,923,303 to Hundt, 3,596,667 to Buercklin, and 3,311,117 to Thompson.

Patents showing devices for other utilities, such as nail buffing, tooth polishing, and callosity removing, describe buffing or grinding surfaces of various shapes with various types of guards. See, for example, U.S. Pat. Nos. 2,840,837 to Gustems, 1,822,631 to Roig, 4,335,480 to Liu and 1,869,197 to Holz. The disclosures of such patents, however, would not suggest their applicability toward the solution of the problems discussed above with respect to powered nail files capable of effective use regardless of the shape, curvature or size of the nail.

Until now, no electric manicuring or pedicuring device has been devised which is capable of allowing access to all portions of the end tip of a fingernail or toenail, regardless of the shape, curvature or size thereof, without damaging the region of skin near the nail by the filing member.

SUMMARY OF THE INVENTION

Accordingly, it is an object of the present invention to eliminate the deficiencies of the prior art, such as those set forth hereinabove.

It is a further object of the present invention to provide an improved electrically powered fingernail or toenail filing device.

It is yet a further object of the present invention to provide such a device which permits ready access to all portions of the end tip of a fingernail or toenail, regardless of the shape, curvature or size thereof.

It is another object of the present invention to provide such a device which will perform in accordance with the previous objects without damaging the region of skin near the nail.

It is still another object of the present invention to provide an improved electrically powered fingernail or toenail filing device shaped to permit easy handling during operation and convenient storability.

These and other objects of the present invention are accomplished through the use of a rotatable filing member having a taper toward the outer tip, preferably of football or pine cone shape. The filing member is powered to rotate about its longitudinal axis by suitable batteries or by being plugged into a standard AC electrical power source. A skin guard is disposed to axially surround at least half of the filing member to protect the skin under the nail during filing operations. The guard also, preferably, extends over the end tip to provide further protection.

Still other objects, features and attendant advantages of the present invention will become apparent to those skilled in the art from a reading of the following detailed description of embodiments constructed in accordance therewith, taken in conjunction with the accompanying drawings.

DESCRIPTION OF PREFERRED EMBODIMENT

Figure 1:
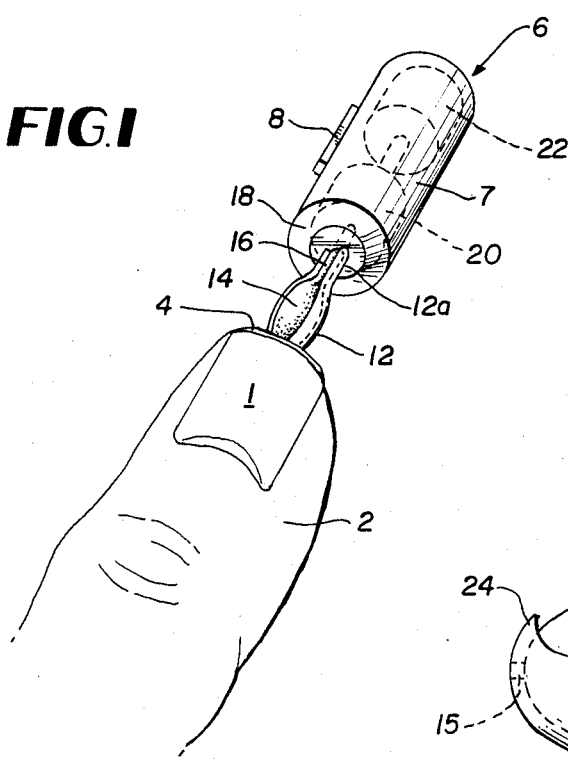
FIG. 1 is a perspective view of the electric nail filing device of the present invention in operational use.

The presently preferred embodiment of the present invention is illustrated in the accompanying drawings. The electric fingernail or toenail filing device 6 includes a body portion 7, preferably cylindrical. One end of the body portion 7 may taper at a frusto-conical portion 18. A rotatable shaft 16 is provided connected to a filing member 14 which is preferably substantially pine cone shaped. The drive shaft 16 and filing member 14 are driven by any suitable means, such as a small D.C. electric motor 20 within the body portion 7 powered, preferably, by a battery 22 and controlled by a suitable on-off switch 8.

The body 7 of the manicuring device is intended to be as small as possible so as to enable easy portability. It is intended that the filing device be carried conveniently in a purse or pocket in the same manner as the ubiquitous nail file. For example, the diameter is preferably under 1 inch and more preferably about 0.5 inch, with a length of no more than about 4 inches. Since the device is lightweight and small, it exhibits good handling maneuverability when in use, as well as convenient portability and storability.

Figure 2:
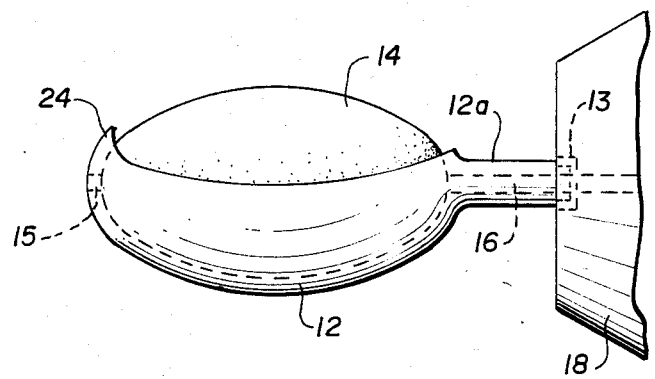
FIG. 2 is a side elevational view of the filing portion of the electric nail filing device of the present invention.
Figure 3:
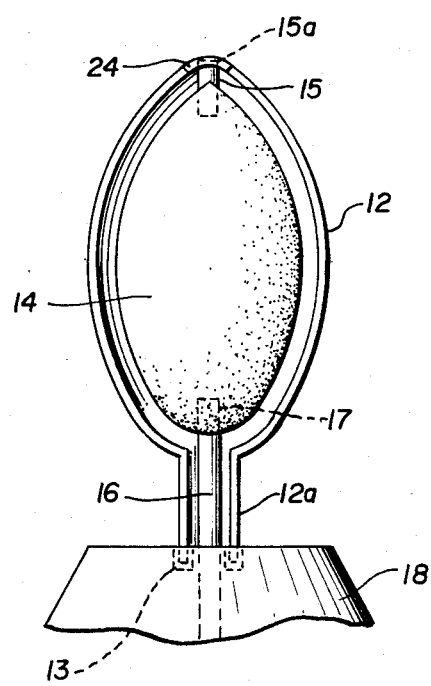
FIG. 3 is a top view of the filing portion of the electric nail filing device of the present invention.
Figure 4:
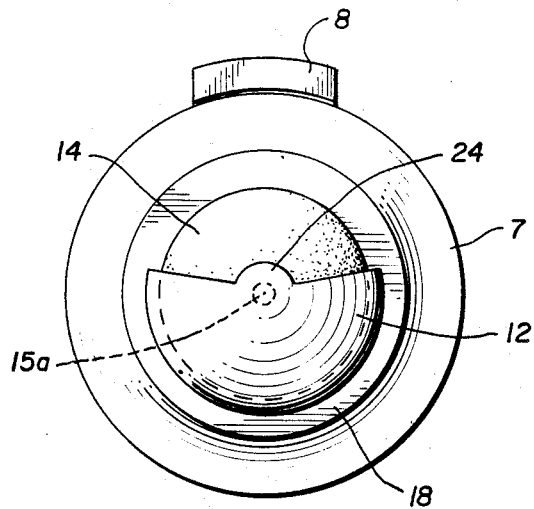
FIG. 4 is an end elevational view of the electric nail filing device of the present invention.

A protective skin guard 12 shields and protects finger or toe 2 from skin damage while the filing member 14 is in operation adjacent the tip 4 of the fingernail or toenail 1. This allows for complete filing of all portions of the nail 1 to achieve a cosmetically perfect nail appearance, regardless of the size, shape or curvature of the nail 1. As shown in FIGS. 2-4, the skin guard 12 is disposed about the filing member 14 so as to house the filing member tip-to-tip longitudinally. The guard 12 preferably surrounds 180° to 260° of the filing member 12 when viewed in a cross-sectional plane normal to the rotational axis. The preferred embodiment, shown particularly in FIG. 4, has the skin guard 12 surrounding about 200° of the filing member 14.

The guard 12 also preferably includes a portion 24 covering the tip end of the filing member 14 to give an additional degree of protection to the skin adjacent the nail during operation.

The protective guard 12 is preferably made of a rigid, thin metal or plastic material to form a smooth shell-like guard disposed as close as possible to the filing member 12 without touching it and leaving sufficient space to allow for some amount of freedom to compensate for any slight movement or distortion during use. However, it should not be disposed so far from the filing member 14 as to unduly enlarge the filing member 14-guard 12 combination. This combination must be sufficiently small in size to allow freedom of movement around the entire nail tip 4.

The skin guard 12 may be attached to the body 6 in any suitable manner which will permit it to serve its intended function. In the embodiment shown in the drawings the guard 12 is provided with a stem portion 12a extending at least half-way around drive shaft 16 and mating with a correspondingly shaped recess 13 in the end of the body portion 7. The guard 12 may further be anchored in place by means of a pin member 15 connected to the tip of the filing member 14 as an extension of the longitudinal axis of the filing member 14. The guard 12 is provided with an aperture 15a which receives the pin member 15, allowing the grinding member to rotate freely within the interior of the guard 12.

The exterior surface of the grinding member 14 includes abrasive material that will allow for the fine filing of the fingernail or toenail. Material such as fine abrasive mineral grit provides such fine filing qualities. The configuration of the exterior surface of the grinding member 14 may itself provide the required filing qualities, such as on the surface of a metal nail file.

While many different materials and surface configurations will provide the desired fine filing properties, all as is well known in the nail filing art, it is critical that the surface configuration not be sharp and damaging such as in the callosity remover of U.S. Pat. No. 1,869,197 to Holz. To accomplish the objects of the present invention the surface must permit fine filing of toenails and fingernails and not cause chipping.

While the preferred shape of the grinding member 14 is substantially pine cone shaped as shown in FIG. 2, the important feature of the chosen shape is a tapering toward the outer tip. The tapering may result in a curved tip as in the pine cone shape illustrated in FIG. 2, or as in an oblong or elliptical solid. The tapering may also result in a pointed tip so that the shape might be that of a football, as in FIG. 3, or a cone. The shape need only taper at the outside end, so the filing member 14 may also have the shape of one-half of a pine cone, football or the like. The tapering tip permits a smaller diameter portion to be used near the side edges of the nails where there is less room between the nail and the skin, and the thicker diameter portion for the remainder of the nail. Whatever the shape of the grinding member 14, the skin guard 12 will have a corresponding shape to surround the desired portion of the grinding member 14 and, optionally, overlay the end tip.

The preferred form of the device of the present invention is compact and battery operated. However, the motor 7 may be driven by standard AC current by being plugged into an AC outlet. This may be desirable in more heavy-duty applications, such as in a professional manicurist's or pedicurist's office. In that case the size, and shape of the body 7 may differ from that described, although the grinding member-skin guard combination will not substantially change.

It will be obvious to those skilled in the art that various other changes and modifications may be made without departing from the scope of the invention and the invention is not to be considered limited to what is shown in the drawings and described in the specification.

What is claimed is:

1. A fingernail or toenail filing device, comprising;
a housing:
a drive shaft extending from said housing;
a drive means disposed within said housing, for rotationally driving said drive shaft;
a filing member, rotatable about a longitudinal axis, having a surface capable of providing fine nail filing when in use and having a shape which is symmetrical about the longitudinal axis thereof, the shape tapering toward one longitudinal end thereof, said filing member being connected to said drive shaft at the end of said filing member opposite said tapering end; and
protective skin guard means, connected to said housing, comprising a thin shell of shaped substantially corresponding to that of said filing member, extending substantially from the end of the longitudinal axis connected to said drive shaft to the tapered end and surrounding about 180° to about 260° around said filing member, as measured in a plane perpendicular to the longitudinal axis, and including a portion substantially covering the tapered end tip of said filing member, said skin guard means being closely adjacent but spaced from said filing member.

2. A nail filing device in accordance with claim 1, wherein said filing member has a fine particulated abrasive surface.

3. A nail filing device in accordance with claim 1, wherein said guard means is made of thin metal or molded plastic.

4. A nail filing device in accordance with claim 3, wherein the exterior surface of said guard means is smooth.

5. A nail filing device in accordance with claim 1, wherein the tapered end of said filing member has a substantially rounded tip.

6. A nail filing device in accordance with claim 5, wherein said filing member is substantially pine cone shaped.

7. A nail filing device in accordance with claim 1, wherein the tapered end of said filing member comes to a point.

8. A nail filing device in accordance with claim 7, wherein said filing member is substantially football shaped.

9. A nail filing device in accordance with claim 1, wherein said drive means comprises an electric motor connected to a source of electrical power.

10. A nail filing device in accordance with claim 1, wherein said source of electrical power is at least one battery disposed within said housing.

* * * * *